United States Patent [19]

Cegla

[11] Patent Number: 5,569,122
[45] Date of Patent: Oct. 29, 1996

[54] THERAPEUTIC DEVICE FOR IMPROVING BREATHING

[76] Inventor: Ulrich Cegla, Rhönstrasse 3, D-56410 Montabauer, Germany

[21] Appl. No.: 435,408

[22] Filed: May 10, 1995

[30] Foreign Application Priority Data

May 11, 1994 [DE] Germany .......................... 44 16 575.7

[51] Int. Cl.⁶ .................................................. A63B 23/18
[52] U.S. Cl. ............................................ 482/13; 128/200.24
[58] Field of Search .......................... 482/13; 128/200.24; 446/202, 207, 208, 209, 216, 416; 601/41, 38

[56] References Cited

U.S. PATENT DOCUMENTS

| | | | |
|---|---|---|---|
| 3,426,477 | 2/1969 | Novaco | 446/208 |
| 3,972,326 | 8/1976 | Brawn | 482/13 |
| 4,062,358 | 12/1977 | Kritzer | 482/13 |
| 4,444,202 | 4/1984 | Rubin et al. | 482/13 |
| 5,234,368 | 8/1993 | Carraway | 446/209 |

FOREIGN PATENT DOCUMENTS

| | | |
|---|---|---|
| 0337990 | 10/1989 | European Pat. Off. . |
| 7302515 | 1/1973 | Germany . |
| 563171 | 5/1975 | Switzerland . |

*Primary Examiner*—Richard J. Apley
*Assistant Examiner*—Jeanne M. Clark
*Attorney, Agent, or Firm*—Robert W. Becker & Associates

[57] ABSTRACT

A therapeutic device, with which during inhalation or exhalation an oscillating air resistance is generated, for improving breathing and expectoration of a patient has a bent tube section with a first and a second end. The tube section has an inner wall surface. A first mouthpiece is connected to the first end. An elastically deformable hose section having a first and a second end, the first end connected to the first mouthpiece, is positioned inside the tube section so as to rest at its inner wall surface. The second end of the elastically deformable hose section is open. To the second end of the tube section a second mouthpiece may be connected.

21 Claims, 2 Drawing Sheets

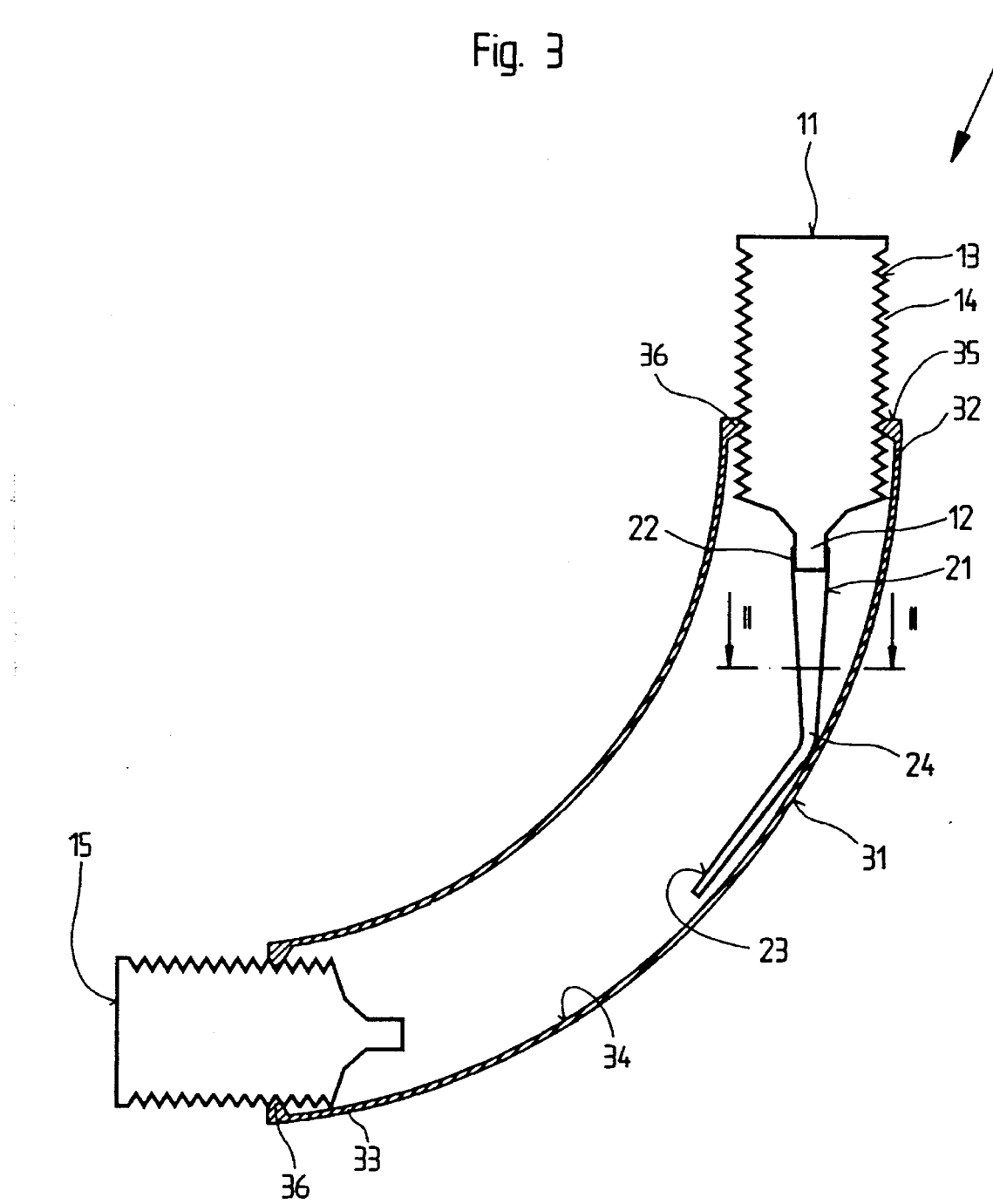

5,569,122

THERAPEUTIC DEVICE FOR IMPROVING BREATHING

BACKGROUND OF THE INVENTION

The present invention relates to a therapeutic device for improving breathing and expectoration of a patient, with which during inhalation or exhalation an oscillating air resistance is generated.

A device of this kind is known from European document 33 79 90 which supports the physical breathing therapy, in particular for venting the lung periphery in case of diseases such as chronic bronchitis, bronchiectasis, mucoviscidosis, lung emphysema etc. Such resistance devices have a first tubular section which is provided with an air inlet opening into which the patient can exhale and a second upwardly bent tubular section provided with a circular conical outlet channel. A ball is loosely placed into the outlet channel and has a diameter that is greater than the smallest diameter of the outlet channel. Before exhaling takes place, the outlet channel is thus closed by the ball, and the air exhaled by the patient lifts the ball and thus presents a resistance due to its own weight to the exhaling action of the patient.

The air pressure generated by exhaling thus moves the ball within the device back and forth so that vibrations and a positive exhaling resistance are generated. However, it is disadvantageous that the outlet channel is often not closed off by the ball. The first tubular section must be maintained substantially horizontally during use by the patient such that the second tubular section is essentially extending vertically upwardly; if this positioning is not ensured a reliable function of the device is not possible. The handling of the device is thus difficult. Furthermore, since with increasing breathing action the resulting breathing pressure is reduced, the outlet channel is sometimes prematurely closed so that despite the physical measure the bronchial passages are also closed at the end of the exhalation action.

It is therefore an object of the present invention to provide a therapeutic device of the aforementioned kind which is not only easy to manipulate and useable in any desired position, but which also generates intrathoracic percussions. The constructive design of the device should be simple so that an economic manufacture is possible. Primarily, it should be possible that during exhalation an oscillating positive exhaling pressure is provided and that different frequencies can be easily adjusted in order to adapt the device to the needs of a patient.

SUMMARY OF THE INVENTION

A therapeutic device, with which during inhalation or exhalation an oscillating air resistance is generated, for improving breathing and expectoration of a patient, according to the present invention is primarily characterized by:

A bent tube section with a first and a second end, the tube section having an inner wall surface;

A first mouthpiece connected to the first end;

An elastically deformable hose section having a first and a second end, the first end of the hose section connected to the first mouthpiece, wherein the hose section is positioned inside the tube section so as to rest at the inner wall surface and wherein the second end of the hose section is open.

Preferably, the first end of the hose section is detachably connected to the first mouthpiece.

Advantageously, the tube section has an angular bent or, in the alternative, is curved.

Expediently, the first mouthpiece is connected to the tube section so as to be displaceable in an axial direction of the tube section.

Preferably, for displacing the first mouthpiece in the axial direction, the first mouthpiece has an outer wall surface provided with recesses axially spaced from one another. The first end of the tube section has at least one projection for engaging the recesses.

Preferably, at least two of the projections are provided and the at least two projections are spaced from one another in a circumferential direction of the tube section.

Advantageously, the hose section has oscillating characteristics which are changeable by displacing the first mouthpiece in the axial direction.

In another embodiment of the present invention the first mouthpiece is connected to the tube section so as to be rotatable relative to the tube section.

Preferably, for displacing the first mouthpiece in the axial direction and rotating the first mouthpiece relative to the tube section, the first mouthpiece has an outer wall surface provided with recesses axially spaced from one another and the first end of the tube section has at least one projection for engaging the recesses.

Preferably, at least two of the projections are provided and the at least two projections are spaced from one another in a circumferential direction of the tube section.

Advantageously, the hose section has oscillating characteristics which are changeable by displacing the first mouthpiece in the axial direction and by rotating the first mouthpiece.

In yet another embodiment of the present invention, the first mouthpiece is connected to the tube section so as to be rotatable relative to the tube section. For rotating the first mouthpiece relative to the tube section, the first mouth piece has an outer wall surface provided with recesses axially spaced from one another and the first end of the tube section has at least one projection for engaging the recesses. Preferably, at least two of the projections are provided and the at least two projections are spaced from one another in a circumferential direction of the tube section.

Expediently, the hose section has oscillating characteristics which are changeable by rotating the first mouthpiece.

In a preferred embodiment of the present invention, the hose section has a rectangular cross-section.

Preferably, the hose section comprises an angled portion for resting at the inner wall surface of the tube section.

Expediently, the device further comprises a second mouthpiece connected to the second end of the tube section.

In a preferred embodiment the device further comprises a closure cap connected to the second end of the tube section. The closure cap is air-permeable or partially open. The closure cap is preferably embodied as a sound absorber.

According to the present invention an elastically deformable hose section is connected, preferably detachably, to a mouthpiece and has a free end which is open. The mouthpiece is inserted into a bent (curved or angularly bent) tube section such that the hose section rests at the inner wall surface of the tube section.

It is expedient that the mouthpiece in the axial direction of the tube section is position-adjustable/displaceable and/or rotatable relative to the tube section. This can be realized in a simple manner by providing the outer wall surface of the mouthpiece with recesses in the form of grooves, notches, indentations, etc. which are spaced at a distance to one another in the axial direction and by providing the end of the tubular section that receives the mouthpiece with one or more projections, for example, in the form of a catch or a nose, that engage the recesses and are distributed over the circumference of the tubular section.

The hose section connected to the mouthpiece should have a rectangular cross-section and should be elastically deformable. The area of the hose section which rests at the inner walls surface of the tube section should be provided with an angled portion.

It is furthermore suggested to provide the free end of the tube section with a further mouthpiece or to provide the free end of the tube section with an air-permeable or partially open closure cap.

A therapeutic device according to the present invention for improving breathing and expectoration of a patient ensures that due to intrathoracic vibrations the bronchial mucus is loosened or liquified without closing the bronchial passages, respectively, the trachea during forced exhalation due to the pressure resulting within the thorax. During exhalation and thus during blowing into the angled hose section inserted into the bent tube section, an oscillating, positive pressure results and, furthermore, the free end of the hose section vibrates within a low frequency range so that, despite the vibration and despite the positive exhalation resistance, a sufficiently high flow velocity within the bronchial tube results and the loosened and liquified mucus can be removed from the bronchial passages.

Another advantage is that during the entire exhalation action an oscillating, positive exhaling pressure is present and that due to a change of the position of the mouthpiece relative to the tube section different frequencies can be easily adjusted. Furthermore, the frequency can be adjusted with the curvature of the tube section as well as with the length of the hose section. By varying the dimensions of the individual components of the therapeutic device as well as by varying its material, the vibration amplitude can be selected and adjusted so that the intrathoracic percussions in the range of the thorax resonance frequencies between 12 and 30 hertz, in which they are especially effective, can be selected and preset. By using different hose sections it is also possible to vary the exhalation pressure and the vibration mass in short time periods and without difficulties. With a simple unproblematic manipulation the inventive therapeutic device is thus useful in various advantageous applications.

BRIEF DESCRIPTION OF THE DRAWINGS

The object and advantages of the present invention will appear more clearly from the following specification in conjunction with the accompanying drawings, in which:

FIG. 3 shows the therapeutic device of FIG. 1 with a second mouthpiece connected to the free end of the tube section.

DESCRIPTION OF PREFERRED EMBODIMENTS

The present invention will now be described in detail with the aid of several specific embodiments utilizing FIGS. 1 through 3.

Figure 1:
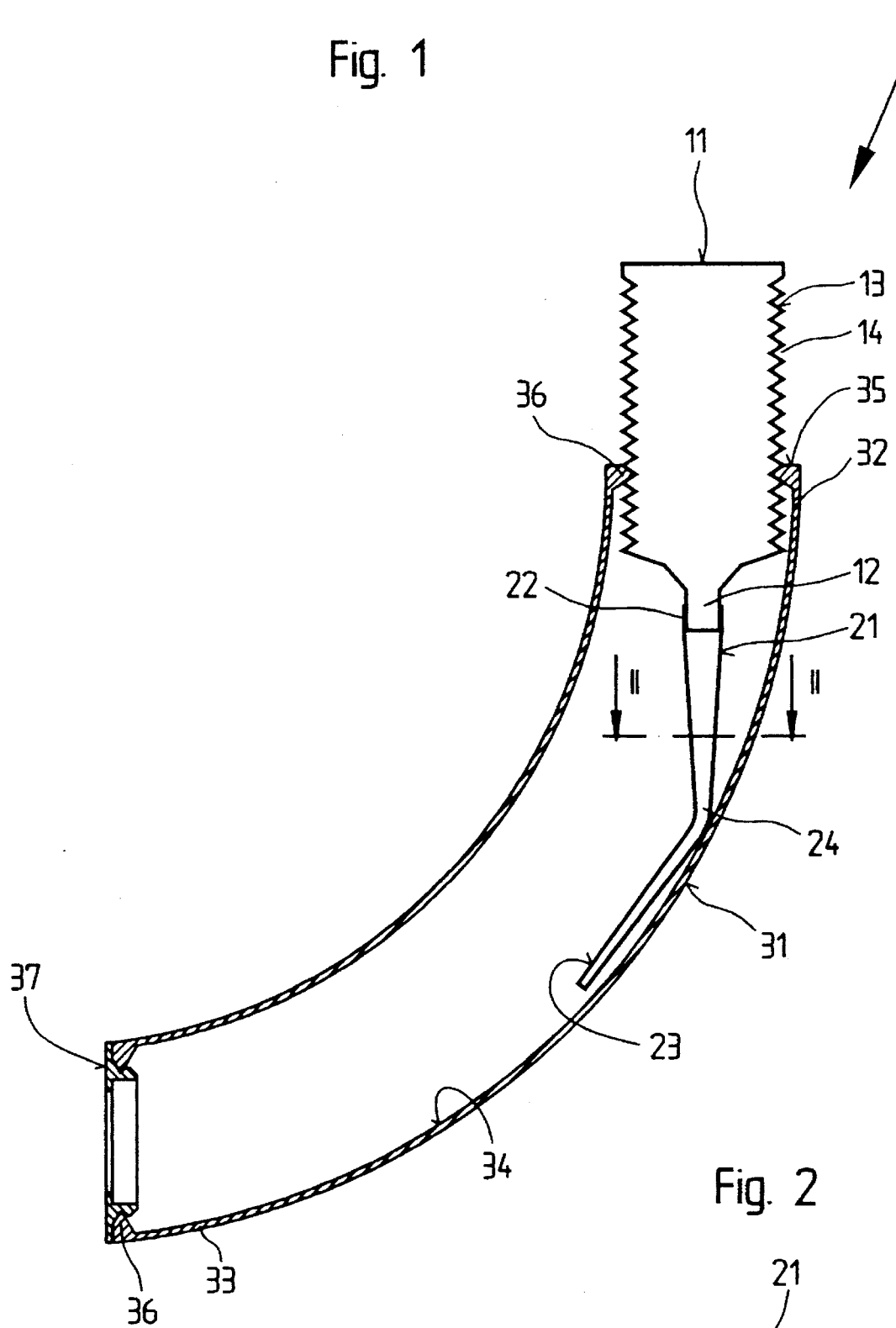
FIG. 1 shows the therapeutic device in longitudinal section comprised of a mouthpiece, and a hose section connected to the mouthpiece and inserted into a bent tube section.
Figure 2:
FIG. 2 shows a section along line II—II of FIG. 1.

The therapeutic device 1 represented in FIG. 1 serves to improve breathing and expectoration of a patient by percussions as well as for venting the lung periphery in the case of illnesses such as chronic bronchitis, bronchiectasis, mucoviscidosis, lung emphysema, etc. It comprised substantially of a mouthpiece 11, to which is detachably connected via a pre-formed projection 12 a hose section 21, and a bent tube section 31 into the free end 32 of which the mouthpiece 11 is inserted. The other end 33 of the tube section 31 is covered by an air-permeable closure cap 37; i.e., the cap 37 is partially open as shown in FIG. 1.

In order to loosen the bronchial mucus with intrathorax vibrations and in order to easily adjust these percussions to the resonance frequency of the thorax, which is between 12 and 30 hertz, the mouth piece 11 is inserted into the tube section 31 so as to be displaceable or position-adjustable. For this purpose, the mouthpiece 11 is provided with recesses in the form of grooves 14 positioned in the axial direction at a distance to one another. The inner wall surface 34 of the tube section 31 in the area of the two ends 32 and 33 is provided with projections 35 in the form of a catch or nose 36 which engage the recesses or grooves 14 of the mouthpiece 11o Furthermore, a hose section 21 is connected with its end 22 to a projection 12 at the mouthpiece 11 and its other end 23 is open. The hose section 21 has a bent portion 24 which is formed by resting at the inner wall surface 34 of the tube section 31.

When the therapeutic device 1 is used by a patient and exhaled air is supplied to the rectangular cross-section of the elastically deformable hose section 21 during exhalation, the therapeutic device 1 generates an oscillating positive pressure and, furthermore, the free end 23 of the hose section 21 begins to vibrate at a low frequency within the range of the resonance frequency of the thorax. The frequency and the blowing pressure can be influenced by adjusting the mouthpiece 11. Thus, the therapeutic device can be adjusted to the needs of a respective patient, and mucus within the bronchial tubes can be loosened so that lung ventilation as well as removal of mucus by coughing can be improved.

For using the therapeutic device during inhalation the free end 33 of the tube section 31 is provided with a further mouthpiece 15 inserted into the free end 33, as shown in FIG. 3. The air to be inhaled is sucked through the opening hose section 21. During inhalation vibration and pressure changes occur that correspond to those resulting from exhaling through the therapeutic device 1. It is also possible to use the therapeutic device 1 for inhalation as well as exhalation. For this purpose, the therapeutic device 1 according to FIG. 3 is used.

Via mouthpiece 15 air is inhaled through the hose section 21. By correspondingly inserting and/or rotating the mouthpiece 11 the hose section 21 rests at the bent tube section 31 and vibrates with a certain frequency.

Before exhaling, the patient must turn around the therapeutic device 1 and exhale the air stored within his lungs through the mouthpiece 11 and the hose section 21.

This suction-pressure-effect during inhalation and exhalation through the therapeutic device 1 improves the stamina muscle training of the breathing muscles. Furthermore, the vibrations during inhalation and exhalation result in a loosening (liquefying) of the bronchial mucus whereby, due to the resulting vibrations, possibly present mucus clots can be simultaneously retracted into the area of the lungs in which there is still a surface active substance present so that during the subsequent exhaling action, respectively, during coughing the mucus can be removed from the bronchial passages.

The present invention is, of course, in no way restricted to the specific disclosure of the specification and drawings, but also encompasses any modifications within the scope of the appended claims.

What I claim is:

1. A therapeutic device, with which during inhalation or exhalation an oscillating air resistance is generated, for improving breathing and expectoration of a patient, said device comprising:

a bent tube section with a first and a second end and an intermediate curved section said tube section having an inner wall surface;

a first mouthpiece connected to said first end;

an elastically deformable hose section having a first and a second end, said first end of said hose section connected to said first mouthpiece, wherein said hose section is positioned inside said tube section so as to rest along said inner wall surface of the intermediate curved section forming a bent portion in said hose section, and wherein said second end, of said hose section is open.

2. A device according to claim 1, wherein said first end of said hose section has a means for detachably connecting said hose section to said first mouthpiece.

3. A device according to claim 1 wherein said tube section is curved.

4. A device according to claim 1, wherein said first mouthpiece has a means for connecting said first mouthpiece to said tube section so as to be displaceable in an axial direction of said tube section.

5. A device according to claim 4, wherein, for displacing said first mouthpiece in the axial direction, said first mouthpiece has an outer wall surface provided with recesses axially spaced from one another and wherein said first end of said tube section has at least one projection for engaging said recesses.

6. A device according to claim 5, wherein at least two of said projections are provided and wherein said at least two projections are spaced from one another in a circumferential direction of said tube section.

7. A device according to claim 4, wherein said hose section has a structure providing oscillating characteristics and wherein the oscillating characteristics are changeable by displacing said first mouthpiece in the axial direction.

8. A device according to claim 4, wherein said first mouthpiece has a means for rotatably connecting said first mouthpiece to said tube section.

9. A device according to claim 8, wherein, for displacing said first mouthpiece in the axial direction and rotating said first mouthpiece relative to said tube section, said first mouthpiece has an outer wall surface provided with recesses axially spaced from one another and wherein said first end of said tube section has at least one projection for engaging said recesses.

10. A device according to claim 9, wherein at least two of said projections are provided and wherein said at least two projections are spaced from one another in a circumferential direction of said tube section.

11. A device according to claim 8, wherein said hose section has a structure providing oscillating characteristics and wherein the oscillating characteristics are changeable by displacing said first mouthpiece in the axial direction and by rotating said first mouthpiece.

12. A device according to claim 1, wherein said first mouthpiece has a means for rotatably connecting said first mouthpiece to said tube section.

13. A device according to claim 12, wherein, for rotating said first mouthpiece relative to said tube section, said first mouthpiece has an outer wall surface provided with recesses axially spaced from one another and wherein said first end of said tube section has at least one projection for engaging said recesses.

14. A device according to claim 13, wherein at least two of said projections are provided and wherein said at least two projections are spaced from one another in a circumferential direction of said tube section.

15. A device according to claim 12, wherein said hose section has a structure providing oscillating characteristics and wherein the oscillating characteristics are changeable by rotating said first mouthpiece.

16. A device according to claim 1, wherein said hose section has a rectangular cross-section.

17. A device according to claim 1, wherein said hose section comprises an angled portion for resting at said inner wall surface of said tube section.

18. A device according to claim 1, further comprising a second mouthpiece connected to said second end of said tube section.

19. A device according to claim 1, further comprising a closure cap connected to said second end of said tube section.

20. A device according to claim 19, wherein said closure cap is air-permeable.

21. A device according to claim 19, wherein said closure cap is partially open.

* * * * *